United States Patent [19]
Fields, Jr. et al.

[11] Patent Number: 6,072,061
[45] Date of Patent: Jun. 6, 2000

[54] PREPARATION OF QUINONEIMINES FROM HYDROXYPHENYLAMINES USING A HYPOCHLORITE AS AN OXIDATION AGENT

[75] Inventors: Donald L. Fields, Jr., Copley; Jayant S. Lodaya, Akron, both of Ohio

[73] Assignee: Flexsys America L.P., Akron, Ohio

[21] Appl. No.: 09/272,346

[22] Filed: Mar. 19, 1999

Related U.S. Application Data

[60] Provisional application No. 60/081,281, Apr. 10, 1998.

[51] Int. Cl.$^7$ .................................................. C07C 50/04
[52] U.S. Cl. ........................................................ 552/302
[58] Field of Search ............................. 564/272; 552/302

[56] References Cited

U.S. PATENT DOCUMENTS

| | | | |
|---|---|---|---|
| 2,170,191 | 8/1939 | Fisher | 18/53 |
| 4,968,843 | 11/1990 | Cottman | 564/397 |
| 5,053,540 | 10/1991 | Cottman | 564/397 |
| 5,068,439 | 11/1991 | Cottman | 564/434 |
| 5,091,545 | 2/1992 | Parker | 552/302 |
| 5,118,807 | 6/1992 | Wheeler | 544/197 |
| 5,189,218 | 2/1993 | Desmurs et al. | 564/272 |

FOREIGN PATENT DOCUMENTS

| | | |
|---|---|---|
| 157 288 | 12/1904 | Germany . |
| 1 267 635 | 3/1972 | United Kingdom . |
| 1267635 | 3/1972 | United Kingdom . |

OTHER PUBLICATIONS

Bouchet et al, Aryl diazo compds and diazonium salts, J. Med. Chem., 1987, 30(12), 2222–7.
*International Search Report*, dated Jun. 16, 1999 (PCT/IB99/00597).
R. Lantz, et al: Bulletin De La Societe Chimique De France, vol. 37, No. 4, May 22, 1925, pp. 890–901 and English Translation.
*Derwent Abstract*, 90–354696/47, Nov. 6, 1990.
*Derwent Abstract*, 91–305160/42, Oct. 16, 1991.
*Abstract*, 95731R, Dec. 23, 1970.
*Search Report*, 13598, dated Feb. 4, 1999.
*Derwent Abstract*, 91–289414/40, Oct. 2, 1991.
Organic Syntheses, R.E. Harman, Chloro-$_p$-Benzoquinone, John Wiley Sons, Inc., Collective vol., 4, pp. 148–154.
*Quinolines and Isoquinolines*, pp. 572–606.
Research Disclosure, 17332, Process of preparing polyaniline amines, Sep. 1978.

*Primary Examiner*—Jose' G. Dees
*Assistant Examiner*—Alton Pryor
*Attorney, Agent, or Firm*—Louis A. Morris

[57] ABSTRACT

A hydroxyphenylamine compound can be converted, with high yield and high selectivity, into its corresponding quinoneimine by reacting the hydroxyphenylamine with a hypochlorite oxidation reactant.

28 Claims, No Drawings

PREPARATION OF QUINONEIMINES FROM HYDROXYPHENYLAMINES USING A HYPOCHLORITE AS AN OXIDATION AGENT

This application claims priority to the filing date of U.S. Provisional Application Ser. No. 60/081,281, filed Apr. 10, 1998.

FIELD OF THE INVENTION

This invention relates to a process for preparing quinoneimines from their corresponding hydroxyphenylamines using a hypochlorite as an oxidation agent.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982.

The synthesis of quinones is well documented. See, for example, J. Cason, *Synthesis of Benzoquinones by Oxidation*, in *Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or from quinic acid. The reagents generally used for the oxidation are dichromate/sulfuric acid mixture, ferric chloride, silver (II) oxide or ceric ammonium nitrate. In these cases, oxidation of the aminoaromatic compound is accompanied by hydrolysis to the corresponding quinone. Some processes may take several hours for completion of the reaction.

Thus, some of the prior art processes utilize a catalytic agent to achieve an acceptable reaction rate while other processes proceed without catalysts. The process according to the present invention utilizes a hypochlorite reagent which provides extremely high conversion, high selectivity, and fast reaction rates to prepare a quinoneimine.

A prior art process which utilizes a catalyst in the preparation of a quinoneimine compound is disclosed by Desmurs, et al. in U.S. Pat. No. 5,189,218. The process of Desmurs, et al., which converts N-(4-hydroxyphenyl)aniline into N-phenylbenzoquinone-imine, utilizes a manganese, copper, cobalt, and/or nickel compound as a catalyst in an oxidation type reaction.

The above process of Desmurs, et al., which uses a metal catalytic component, along with any other processes which utilize a metal catalyst, have several drawbacks. Not only are the metal catalysts relatively expensive, they raise important environmental concerns. For example, effluent streams and products can be contaminated by the metals. Further, recovery of the catalyst for reuse can be prohibitively expensive.

Other processes are known which use oxidizing agents to convert phenylenediamines into their corresponding quinonediimines. For example, EP 708,081 (Bernhardt et al), which describes the conversion of phenylenediamines to phenylenediimines by oxidation of the diamine in an alkali/alcoholic solution, gives a general description of such processes in its background. The EP '081 process suffers from various disadvantages including long reaction times and low yields.

An oxidation process for the catalytic oxidation of hydroxy containing aromatic compounds to form their respective quinone compounds is described by Parker in U.S. Pat. No. 5,091,545. Parker teaches the use of catalytic cobalt, a primary aliphatic amine and an alcohol to convert a hydroxy containing aromatic compound to the corresponding quinone compounds.

Additional oxidation conversion processes are described by Wheeler in U.S. Pat. No. 5,118,807, by GB 1,267,635, and by Haas et al, in EP 708,080. However, the use of a hypochlorite as an oxidizing agent in the conversion of hydroxyphenylamine compounds to give highly selective yields of N-substituted-quinoneimine compounds has not heretofore been suggested.

As such, the current invention is based on the problem of providing a simple and economic process for the preparation of N-substituted-quinoneimines in high yields and with high selectivity.

SUMMARY OF THE INVENTION

It has been discovered that hydroxyphenylamine compounds can be converted with extremely high selectivity into the corresponding quinoneimine by reaction of the hydroxyphenylamine with a hypochlorite oxidant. Conditions are revealed in which nearly quantitative yields have been obtained.

In contrast to prior art, an advantage of the present invention is that the conversion of hydroxyphenylamine to the corresponding quinoneimine is nearly quantitative. Thus, very little waste material remains upon completion of the reaction.

Another advantage comes from the use of the hypochlorite oxidizing agent. The hypochlorite oxidizing agent avoids the drawbacks associated with metal catalysts which include high cost, product contamination and environmental waste concerns.

An addtional advantage is that the hypochlorite oxidizing agents, as set forth herein, provide an extremely high conversion, high selectivity and faster more complete reaction compared to prior art processes.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for converting hydroxyphenylamines into their corresponding quinoneimines.

In accordance with the object of the invention, a hydroxyphenylamine (ortho or para) according to Formula Ia or Ib:

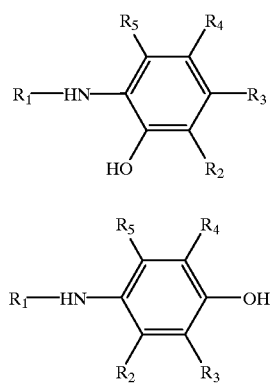

Formula Ia

Formula Ib wherein $R_1$ is selected hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_1$ groups may be linear or branched and each of the $R_1$ groups may be further substituted where appropriate; further wherein $R_2$, $R_3$, $R_4$, and $R_5$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted where appropriate, further wherein adjacent $R_2$, $R_3$, $R_4$, and $R_5$ groups may join to form a poly-cyclic ring system; is reacted with a hypochlorite oxidizing agent.

The reaction produces a corresponding quinoneimine according to Formula IIa or IIb:

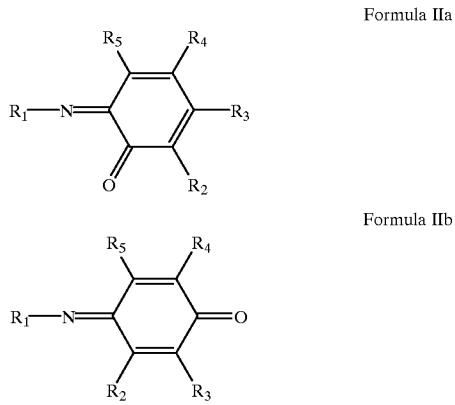

Formula IIa

Formula IIb wherein $R_1$, $R_2$, $R_3$, $R_4$, and $R_5$ are the same as in the compound according to Formula Ia or Ib.

The reaction is represented as follows:

Reaction Scheme 1

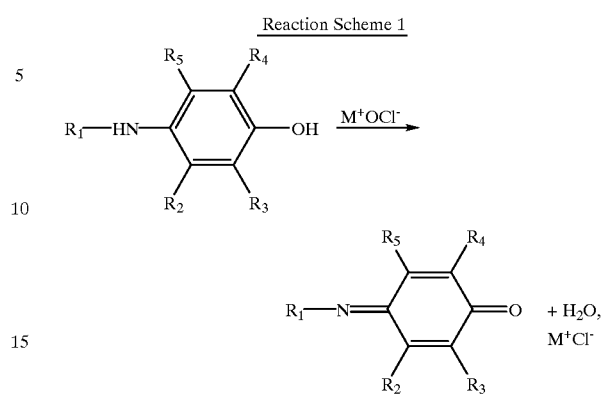

More particularly, the $R_1$ variables are selected from hydrogen, hydroxyl, C1–C50 alkyl, C1–C50 alkoxy, C6–C40 aryloxy, C2–C50 alkenyl, C3–C20 cycloalkyl, C6–C40 aryl, C7–C50 aralkyl, C7–C50 alkaryl, C1–C20 alkylamino, C6–C40 arylamino, C3–C30 heterocyclic containing one or more N, O, S, or P atoms, C1–C50 acyl, aroyl, cyano, halogen such as F, Br, I, or Cl, thiol, C1–C50 thioalkyl, C6–C40 thioaryl, amino, nitro, sulfonate having the formula $SO_3X$ wherein X is selected from sodium, C1–C50 alkyl, or C6–C40 aryl, sulfone, sulfonamide, carboxylic acid, C1–C50 alkyl ester and, C6–C40 aryl ester, wherein the alkyl moieties in the $R_1$ groups may be linear or branched and each of the $R_1$ groups may be further substituted where appropriate; further wherein $R_2$, $R_3$, $R_4$, and $R_5$ are the same or different and are selected from hydroxyl, C1–C50 alkyl, C1–C50 alkoxy, C6–C40 aryloxy, C2–C50 alkenyl, C3–C20 cycloalkyl, C6–C40 aryl, C7–C50 aralkyl, C7–C50 alkaryl, C1–C20 alkylamino, C6–C40 arylamino, C3–C30 heterocyclic containing one or more N, O, S, or P atoms, C1–C50 acyl, aroyl, cyano, halogen such as F, Br, I, or Cl, thiol, C1–C50 thioalkyl, C6–C40 thioaryl, amino, nitro, sulfonate having the formula $SO_3X$ wherein X is selected from sodium, C1–C50 alkyl, or C6–C40 aryl, sulfone, sulfonamide, carboxylic acid, C1–C50 alkyl ester and, C6–C40 aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted where appropriate; further wherein the adjacent $R_2$, $R_3$, $R_4$, and $R_5$ groups may join to form poly-cyclic ring systems including aryl ring systems such as naphthyl, anthracyl, and the like, and heteroaryl ring systems containing one or more N, O, S, or P atoms.

Examples of satisfactory radicals for $R_1$, $R_2$, $R_3$, $R_4$, and $R_5$ are linear or branched alkyls such as methyl, ethyl, propyl, butyl, pentyl, hexyl, heptyl, octyl, nonyl, decyl, dodecyl, and the like; aryls such as phenyl, naphthyl, anthracyl, tolyl, ethylphenyl, 1-ethyl-3-methylpentyl, 1-methylheptyl, and the like; cycloalkyls such as cyclobutyl, cyclopentyl, cyclohexyl, cyclooctyl, and the like. Other examples include allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, caproyl, 3-mercaptopropionyl, benzoyl, phthaloyl, terephthaloyl, aminocarbonyl, carbethoxy, carbonyl, formyl, and the like. These are merely exemplary radicals and are in no way intended to limit the scope of the invention.

Hypochlorite agents include, but are not limited to, metal salts of hypochlorite, chlorate, perchlorate as well as organic hypochlorites such as t-butyl hypochlorite. In reaction scheme 1, as set forth above, M is selected from various metals such as sodium (Na), potassium (K), and calcium (Ca), or various organic groups such as alkyl, aryl and the like. The hypochlorite may be present in amounts ranging from 0.1 to 100 preferably 0.3 to 5 equivalents per equivalent of hydroxyphenylamine. Using less than one equivalent of hypochlorite per equivalent of hydroxyphenylamine allows one to produce blends of quinoneimine and unreacted hydroxyphenylamine. When using more than one equivalent of hypochlorite, it is acceptable to recycle the unreacted hypohlorite stream.

It is additionally contemplated that sodium hypochlorite can be made in situ by passing chlorine through sodium hydroxide solution. For example, one can have a reactant mixture of 4-hydroxyphenylamine and sodium hydroxide and then add chlorine gas to the reactor in known amounts and make sodium hypochlorite in situ. This would, in turn, react with 4-hydroxyphenylamine to give N-phenyl-quinoneimine.

The reaction, according to the present invention, may take place in a solvent system. Various polar and non-polar solvents may be used in the oxidation reaction including various hydrocarbon based solvents and water. Organic solvents useable in the process of the present invention include, but are not limited to, alcohols such as methanol, ethanol, propanol, isopropanol, methyl isobutyl carbinol, ethylene glycol; ketones such as acetone, cyclohexanone, 4-methyl-2-pentanone (methyl isobutyl ketone), 5-methyl-2-hexanone, methyl ethyl ketone; aliphatic and aromatic hydrocarbons as such as hexanes, heptanes, toluene, xylenes; nitrites such as acetonitrile; halogenated solvents such as chloroform, dichloromethane, carbon tetrachloride; water soluable solvents such as dimethyl sulphoxide, N-methyl-2-pyrrolidone, sulfolane, dimethylformamide; esters such as ethyl acetate; ethers such as 1,4-dioxan and mixtures thereof. Water may also be used in the solvent systems alone or as a mixture with the organic solvent. The initial hydroxyphenylamine concentration may range in amounts of from 1% to 100% w/v. Polar solvents may be used alone or in admixture with non-polar solvents to increase the rate of the reaction.

The present reaction may also take place in a neat system, without any solvent added. In a neat system, the hydroxyphenylamine starting material is mixed with the hypochlorite and the mixture is stirred until completion of the reaction. The use of the neat system avoids the handling and flammability hazards associated with the use of solvents, especially the flammability hazards present when a solvent is used in an oxidation reaction.

The present reaction may take place at temperatures from −200° C. to 150° C., preferably from about 0° C. to about 100° C., depending on the solvent.

With water immiscible solvents it is advantageous to utilize a phase transfer catalyst to accelerate the rate of reaction in the process of the present invention. Phase transfer catalysts useable in the present invention include, but are not limited to, quaternary ammonium salts, such as tetramethyl ammonium hydroxide, tetra alkyl ammonium halides, tetra-N-butyl ammonium bromide, tetra-N-butyl ammonium chloride, benzyltriethyl ammonium chloride; phosphonium salts such as bis[tris(dimethylamino) phosphine]iminium chloride; crown ethers and polyethylene glycols.

A phase transfer catalyst can be added directly to the reaction mixture or it can be dissolved in one of the reagents such as hypochlorite or 4-hydroxyphenylamine. The phase transfer catalyst may also be dissolved in a solvent used in the process or in water before addition to the reaction mass.

Another means by which the rate of recation may be increased is through increasing the stirring or mixing rate in the reaction. By increasing the stirring or mixing, the reaction rate may be effectively adjusted to proceed at a faster pace when necessary.

Agents such as sodium sulfite or other neutralizing agents can be added before the workup of the reaction mixture to neutralize any excess of hypochlorite if present in the mixture.

The present invention can be more clearly illustrated by the following examples.

EXAMPLE 1

A solution of 4-hydroxydiphenylamine (2.0 g, 0.011 moles) and acetonitrile (35 mL) was stirred at room temperature. Sodium hypochlorite was then added to this solution(5.8 g, conc.=approx 13%). The mixture was stirred at room temperature for 0.5 hr and then analyzed by HPLC for the consumption of starting material. HPLC area % analysis indicated the formation of the corresponding N-phenyl-p-benzoquinone-imine (NPQI) at 87.5% and 4-hydroxydiphenylamine to be 12.1%. Then an additional amount of sodium hypochlorite (0.9 g, conc.=13%) was added and the reaction mixture was stirred for another 0.5 hrs and then analyzed by HPLC (area % Product, NPQI= 98.9% and 4-hydroxydiphenylamine=0.78%).

A variety of isolation techniques can be used to isolate the product. The technique used in the present example consisted of addition of 10 mL of water (the amount can be adjusted so that the salts will stay in solution and the product can be filtered effectively) and concentration of the reaction mass to remove acetonitrile. The resulting slurry was then filtered to give solids and the solids were washed with water. The solids were isolated in almost quantitative yield and identified as N-Phenyl-p-benzoquinone-imine. If excess sodium hypochlorite is employed in the reaction, it can be neutralized by the addition of an appropriate amount of sodium sulfite at the end of reaction. Other isolation techniques can also be used.

EXAMPLE 2

A solution of 4-hydroxydiphenylamine (5.0 g, 0.027 moles) and toluene (100 mL) was stirred at room temperature. Sodium hypochlorite was then added to this solution (179, conc.=approx 13%) in about 20 minutes using a pump. The mixture was stirred at room temperature for 0.5 hr and then analyzed by HPLC for the consumption of starting material. HPLC area % analysis indicated the formation of the corresponding N-phenyl-p-benzoquinone-imine (NPQI) at 99.4 % and 4-hydroxydiphenylamine to be 0.25%.

A variety of isolation techniques can be used to isolate the product. The technique used in the present example consisted of addition of 20 mL of water (the amount can be adjusted so that the salts will stay in solution and the product can be filtered effectively) and concentration of the reaction mass to remove toluene followed by filtration leading to solids. The solids were washed with water and isolated in almost quantitative yields and identified as N-Phenyl-p-benzoquinone-imine. If excess sodium hypochlorite is employed in the reaction, it can be neutralized by the addition of an appropriate amount of sodium sulfite at the end of reaction. Other isolation techniques can also be used.

EXAMPLE 3

A solution of 4-hydroxydiphenylamine (2.0 g, 0.011 moles) and chloroform (35 mL) was stirred at room temperature. Sodium hypochlorite was then added to this solution (8.2 g, conc.=approx 11%). The mixture was stirred at room temperature for 0.5 hr and then analyzed by HPLC for the consumption of starting material. HPLC area % analysis indicated the formation of the corresponding N-phenyl-p-benzoquinone-imine (NPQI) at 95.6%. After stirring for an additional 0.5 hrs the mixture was analyzed by HPLC again. HPLC area % analysis indicated the formation of the corresponding N-phenyl-p-benzoquinone-imine (NPQI) at 100%. A variety of isolation techniques can be used to isolate the product as mentioned previously.

EXAMPLE 4

A mixture of 4-Hydroxydiphenylamine (3.0 g, 0.0162 moles), acetonitrile (125 mL), sodium hydroxide (3.5 g 50% NaOH solution) and water (10 g) was stirred using a mechanical stirrer at room temperature. Chlorine was passed through this mixture in a controlled fashion and in controlled amounts. After stirring for 0.5 hr, the mixture was analyzed by HPLC. HPLC area % analysis indicated the formation of the corresponding N-phenyl-p-benzoquinone-imine (NPQI) at 85% and 4-hydroxydiphenylamine to be 10.1%. By passing an additional amount of chlorine through the mixture, the rest of the 4-hydroxydiphenylamine can be converted to the corresponding N-phenyl-p-benzoquinone-imine. As mentioned previously, a variety of isolation techniques can be used to isolate the product.

In the case of a process using sodium hypochlorite, a product can be made consisting of various combinations of hydroxyphenylamines and quinone-imines.

As per this process one can make a mixture containing as little as, for example, 1% NPQI to 100% NPQI and 99% to 1% 4-Hydroxydiphenylamine simply by adjusting the charge of hypochlorite or chlorine. This process allows for the design of a desired composition just by controlling the amounts of reactants. The following example illustrates this point clearly:

EXAMPLE 5

A solution of 4-hydroxydiphenylamine (2.0 g, 0.011 moles) and acetonitrile (40 mL) was stirred at room temperature. Sodium hypochlorite was then added to this solution in small increments and the mixture was analyzed by HPLC after 0.5 hrs at room temperature for the consumption of starting material. The procedure was repeated until almost all of the 4-hydroxydiphenylamine was converted to the corresponding NPQI. Analysis indicated consumption of 4-hydroxydiphenylamine and the formation of the corresponding quinone-imine in high selectivity. The results of HPLC area % analysis are summarized in the following table

| Sample # | Area % 4-Hydroxydiphenylamine | Area % NPQI |
| --- | --- | --- |
| 1 | 56.5 | 42.7 |
| 2 | 40.8 | 58.9 |
| 3 | 31.4 | 67.6 |
| 4 | 21.2 | 76.4 |
| 5 | 10.9 | 86.1 |
| 6 | 0.41 | 99.34 |

Again, as set forth in the preceding examples, a variety of isolation techniques can be used to isolate the product. The technique used in the present example consisted of addition of 10 mL of water (the amount can be adjusted so that the salts will stay in solution and the product can be filtered effectively) and concentration of the reaction mass to remove acetonitrile. The resulting slurry was then filtered to give solids and the solids were washed with water. The solids were isolated in almost quantitative yield and identified as N-Phenyl-p-benzoquinone-imine. If excess sodium hypochlorite is employed in the reaction, it can be neutralized by the addition of an appropriate amount of sodium sulfite at the end of reaction. Other isolation techniques can also be used.

As demonstrated in the examples provided above, the reaction has been shown to be carried out in water miscible solvents such as acetonitrile and water immiscible solvents such as toluene. The reaction is very clean and the quinoneimine end product can be obtained in very high yields with high selectivity. Various methods for increasing reaction rates include increasing stirring, addition of polar solvents to the reaction, and addition of phase transfer catalysts to the reaction.

EXAMPLE 6

A solution of 4-hydroxydiphenylamine (2.0 g, 0.011 moles) and heptane (35 mL) was stirred at room temperature. Sodium hypochlorite (8.0 g, conc.=approx 11%) was added to this solution. The mixture was stirred at room temperature for 1 hr and then analyzed by HPLC for the consumption of starting material. HPLC area % analysis indicated the formation of the corresponding N-Phenyl-p-benzoquinone-imine (NPQI) at greater than 99%.

A variety of isolation techniques can be used to isolate the product. The technique used in the present example consisted of addition of 10 mL of water (amount can be adjusted so that the salts will stay in solution and the product can be filtered effectively) to the reaction mixture followed by filtration of the resulting slurry to give solids which were washed with water. HPLC area % analysis of the solids was found to be greater than 99% of the corresponding N-Phenyl-p-benzoquinone-imine (NPQI). The filtrate which resulted in two layers, heptane and an aqueous layer, can be separated and the heptane layer can be recycled back. Other conventional isolation techniques can also be used.

Quinoneimines exhibit multiple activities in vulcanized elastomers. Such activities include long term antioxidant activity. In fact, the antioxidant capacity of the quinoneimine antidegradants persists even after the vulcanizate has been extracted with solvents. In addition, quinoneimines provide the beneficial antioxidant activity without the negative effect on scorch generally associated with other antidegradants common to the industry. Quinoneimines have also been used to modify dynamic-mechanical properties of a vulcanizate. Further, the quinoneimines, and their derivatives, can be used in the preparation of other organic compounds.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, it is claimed:

1. A highly selective process for preparing a quinoneimine by reacting the corresponding hydroxyphenylamine with a hypochlorite oxidizing agent wherein the hydroxyphenylamine is of the following Formula I:

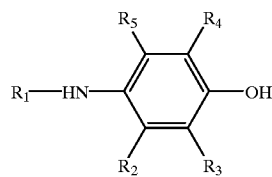

wherein $R_1$ is hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_1$ groups may be linear or branched and each of the $R_1$ groups may be further substituted; further wherein $R_2$, $R_3$, $R_4$, and Rs are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted and further wherein the resulting corresponding quinoneimine is of the following Formula II:

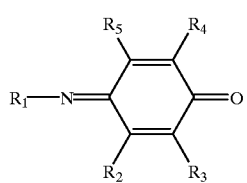

Formula II wherein $R_1$, $R_2$, $R_3$, $R_4$, and $R_5$ are the same as in the compound of Formula I.

2. The process of claim 1 wherein the hypochlorite is of the formula $M^+OCl^-$ wherein M is selected from a metal or an organic group.

3. The process of claim 2 wherein the hypochlorite is sodium hypochlorite (NaOCl).

4. The process of claim 1 wherein $R_1$=phenyl, naphthyl or anthracyl.

5. The process of claim 1 wherein $R_1$=phenyl, $R_2$=hydrogen, $R_3$=hydrogen, $R_4$=hydrogen and, $R_5$=hydrogen.

6. The process of claim 1 wherein $R_1$, $R_2$, $R_3$, $R_4$, and $R_5$ are selected from isopropyl, sec-butyl, cyclohexyl, phenyl, tolyl, 1,4-dimethylpentyl, naphthyl, 1-ethyl-3-methylpentyl, 1-methylheptyl, and hydrogen.

7. The process of claim 1 wherein the reaction takes place in the presence of a solvent.

8. The process of claim 7 wherein the solvent is selected from ketones, alcohols, nitriles, aliphatic and/or aromatic alkanes, aliphatic and/or aromatic alkenes, hydrocarbon solvents, water, and mixtures thereof.

9. The process of claim 7 wherein the solvent is selected from water, t-butyl alcohol, hexanes, acetonitrile, xylenes, heptanes, toluene, methanol, acetone, methyl isobutyl carbinol, chloroform, and methyl isobutyl ketone; each alone or in admixture.

10. The process of claim 7 wherein the solvent comprises a polar solvent and a non-polar solvent, further wherein the polar solvent increases the rate of reaction of the process.

11. The process of claim 1 wherein the reaction takes place in a neat system.

12. The process of claim 1 further comprising addition of a polar solvent in an amount which increases the rate of the reaction.

13. The process of claim 1 further comprising adding a phase transfer catalyst to the reaction to increase the reaction rate.

14. The process of claim 13 wherein the phase transfer catalyst is selected from quaternary ammonium salts, phosphonium salts, crown ethers, and polyethylene glycols.

15. The process of claim 13 wherein the phase transfer catalyst is tetra-N-butyl ammonium bromide.

16. The process of claim 1 wherein the reactants are mixed or stirred together, further wherein the reaction rate may be increased by increasing the mixing or stirring rate.

17. The process of claim 1 wherein the rate of reaction can be increased by increasing the strength (concentration) of the hypochlorite used.

18. A product prepared by the processs of claim 1 wherein the product obtained from the reaction of the process comprises greater than 90% quinoneimine.

19. The process of claim 1 wherein the hypochlorite is made in situ by mixing an alkali metal hydroxide with the hydroxyphenylamine to form an initial reaction mixture and subsequestly passing chlorine through the initial reaction mixture.

20. A process for preparing a quinoneimine from a corresponding hydroxyphenylamine wherein the hydroxyphenylamine is a para-hydroxyphenylamine of the following Formula I:

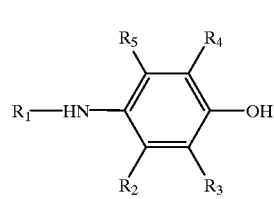

Formula I wherein $R_1$ is hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_1$ groups may be linear or branched and each of the $R_1$ groups may be further substituted; further wherein $R_2$, $R_3$, $R_4$, and $R_5$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted and further wherein the resulting quinoneimine is of the following Formula II:

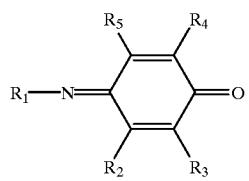

Formula II wherein $R_1$, $R_2$, $R_3$, $R_4$, and $R_5$ are the same as in the compound of Formula I; the reaction taking place by combining at least one compound of Formula I with sodium hypochlorite in the presence of a solvent system further wherein the reaction takes place at a temperature of from about −200° C. to 150° C.

21. The process according to claim 20 wherein water is further present in the solvent system.

22. The process according to claim 20 wherein the solvent system comprises a polar solvent and a non-polar solvent, further wherein the polar solvent increases the rate of reaction of the process.

23. The processs of claim 20 wherein the sodium hypochlorite is present in an amount of from about 0.1 to 100 equivalents hypochlorite per equivalent of hydroxyphenylamine.

24. The process of claim 23 wherein the sodium hypochlorite is present in an amount of from about 0.3 to 5 equivalents hypochlorite per equivalent of hydroxyphenylamine.

25. The process of claim 20 wherein the solvent is selected from water, ketones, alcohols, nitriles, aliphatic and/or aromatic alkanes, aliphatic and/or aromatic alkenes, hydrocarbon solvents and mixtures thereof.

26. The process of claim 20 wherein $R_1$=phenyl, $R_2$=hydrogen, $R_3$=hydrogen, $R_4$=hydrogen and, $R_5$=hydrogen.

27. The process of claim 20 wherein $R_1$, $R_2$, $R_3$, $R_4$, and $R_5$ are selected from isopropyl, sec-butyl, cyclohexyl, phenyl, tolyl, 1,4-dimethylpentyl, naphthyl, 1-ethyl-3-methylpentyl, 1-methylheptyl, and hydrogen.

28. The process according to claim 20 wherein the hydroxyphenylamine component consist essentially of of a mixture of two or more hydroxyphenylamines of formula I.

* * * * *